United States Patent [19]

Yoshioka et al.

[11] 4,279,996

[45] Jul. 21, 1981

[54] KERATIN HYDROLYZATE USEFUL AS HAIR FIXATIVES

[75] Inventors: Issei Yoshioka, Hirakata; Yoichi Kamimura, Osaka, both of Japan

[73] Assignee: Seiwa Kasei Co., Ltd., Osaka, Japan

[21] Appl. No.: 78,850

[22] Filed: Sep. 25, 1979

[30] Foreign Application Priority Data

Oct. 9, 1978 [JP] Japan .................................. 53-124289
Dec. 1, 1978 [JP] Japan .................................. 53-149279
Dec. 29, 1978 [JP] Japan .................................. 53-163085

[51] Int. Cl.$^3$ .............................................. C12P 21/06
[52] U.S. Cl. .................................... 435/69; 435/272; 424/70; 424/72
[58] Field of Search ................ 424/70, 72; 435/68–70, 435/272

[56] References Cited

U.S. PATENT DOCUMENTS 3,578,461  5/1971  Weeks et al. ...................... 435/69 X

FOREIGN PATENT DOCUMENTS 53-119900  10/1978  Japan .

OTHER PUBLICATIONS

Derwent Abstract 84857A of Japanese Unexamined Publication 119900 published Oct. 19, 1978.

*Primary Examiner*—Lionel M. Shapiro
*Attorney, Agent, or Firm*—Armstrong, Nikaido, Marmelstein & Kubovcik

[57] ABSTRACT

Water-soluble keratin hydrolyzate having at least two mercapto groups in one molecule and having an average molecular weight of 2,000 to 20,000, suitable for cosmetic application to the hair, particularly as hair fixatives. The hydrolyzate is prepared by reducing keratin in an aqueous solution of a reducing agent under alkaline conditions and subjecting the resulting reduction product to enzymatic hydrolysis.

7 Claims, 4 Drawing Figures

KERATIN HYDROLYZATE USEFUL AS HAIR FIXATIVES

BACKGROUND OF THE INVENTION

The present invention relates to a water-soluble keratin hydrolyzate, and more particularly to a water-soluble keratin hydrolyzate suited for use in hair-fixing.

In general, cold waving is conducted by employing a waving lotion for first stage which contains a reducing agent such as thioglycollic acid or cysteine and is adjusted to pH about 9 to about 10 with an alkaline material, and a neutralizing lotion for second stage which contains an oxidizing agent such as sodium bromate or hydrogen peroxide. The waving lotion is applied to the hair to permeate into the hair, and the hair is adequately wound and fixed to rods so as to provide the hair with curl as a result of severance of disulfide linkages by the reducing agent. The neutralizing lotion is then applied to the hair so as to newly form disulfide linkages by the oxidizing agent in the state that the hair is set and to provide the hair with permanent wave.

In this cold waving process, it is necessary to employ an alkaline solution in the first stage to make the hair swell and, therefore, the hair and a head of skin are damaged by an alkaline material. Also, upon the oxidation in the second stage, a side reaction takes place partly to form keratin—S—S—CH$_2$COOH linkages, and as a result, the hair is greatly damaged, since, though disulfide linkages are formed again between the keratin molecules, the formation is insufficient.

Such a conventional cold waving process has the disadvantages as stated above, and there is demanded hair fixatives which can produce an excellent waving effect suffering nothing by comparison with a conventional cold waving solution without damaging the hair and skin.

SUMMARY OF THE INVENTION

It is an object of the present invention to provide a material suited for cosmetic application to the hair.

A further object of the invention is to provide a material useful as hair fixatives which can produce an excellent waving effect on the hair without damaging it.

A still further object of the invention is to provide a process for preparing the material suited for cosmetic application to the hair.

Another object of the invention is to provide a cosmetic composition for fixing the hair which can produce an excellent waving or setting effect on the hair without damaging the hair.

These and other objects of the present invention will become more apparent from the description hereinafter.

In accordance with the present invention, there is provided a water-soluble keratin hydrolyzate useful as hair fixatives, having at least two mercapto groups in one molecule and having an average molecular weight of 2,000 to 20,000.

The present invention also provides a process for preparing a water-soluble keratin hydrolyzate which comprises reducing keratin in an aqueous solution of a reducing agent selected from the group consisting of mercaptans and sulfides under alkaline conditions and subjecting the resulting reduction product to enzymatic hydrolysis in an aqueous medium in the presence of an enzyme capable of hydrolyzing protein.

The keratin hydrolyzate of the present invention has an excellent effect in fixing or setting the hair, and can be formulated into various cosmetic compositions intended for application to the hair.

DETAILED DESCRIPTION

Figure 1:
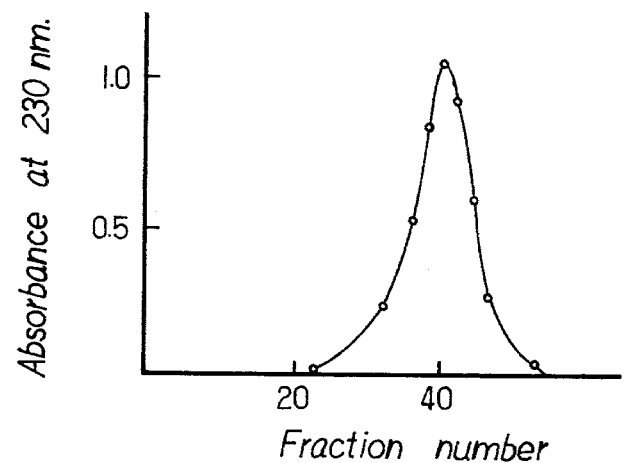
FIG. 1 is a graph showing the relationship between fractions of the eluate in gelfiltration of an aqueous solution of the keratin hydrolyzate and absorbances of the fractions at 230 nm.

The keratin hydrolyzate is prepared by conducting the reduction of keratin with a reducing agent such as a mercaptan or a sulfide under alkaline conditions, by which disulfide linkages of keratin are severed to produce mercapto groups, and then subjecting the resulting reduction product to enzymatic hydrolysis, by which the peptide linkages are severed to lower the molecular weight. The degree of hydrolysis is suitably controlled so that the obtained hydrolyzate has the solubility in water and also has at least two mercapto groups in one molecule.

The thus obtained hydrolyzate of the present invention, i.e. the water-soluble keratin hydrolyzate having at least two mercapto groups in one molecule and an average molecular weight of 2,000 to 20,000 has remarkable characteristics, particularly suitable in cosmetic application to the hair. That is to say, the keratin hydrolyzate of the invention has a film-forming property, and moreover becomes insoluble in water by the oxidation of mercapto groups in the hydrolyzate by oxygen in air to form disulfide linkages between the adjacent molecules of the hydrolyzate. By the formation of disulfide linkages, the adjacent molecules cross-link one after another to form a water-insoluble high polymer. The oxidation may be accelerated by the use of a water-soluble metal compound such as iron gluconate as a catalyst or the use of a peroxide compound such as hydrogen peroxide as an oxidizing agent.

Therefore, when the keratin hydrolyzate is applied or sprayed in the form of a dilute aqueous solution to the hair, and after winding the hair round rods, is dried or oxidized with an oxidizing agent, the mercapto group of a keratin hydrolyzate molecule is oxidized to cross-link and form a disulfide linkage with the mercapto group of another keratin hydrolyzate molecule, and a water-insoluble high polymer film is formed on the hair in the state that the hair is curled.

Moreover, since the keratin hydrolyzate has amino groups and carboxyl groups in its molecule and they make ionic bonds with carboxyl groups and amino groups of the hair respectively, the keratin hydrolyzate strongly fixes to the hair. Therefore, even if the hair is washed with water, the keratin hydrolyzate does not come out with ease in cooperation with change into a water-insoluble high polymer.

Since the water-soluble keratin hydrolyzate of the present invention cross-links and forms a water-insoluble film on the curled hair, it is possible to employ it as a hair fixative for cold waving instead of conventional hair fixatives for cold waving consisting of the combination of a reducing agent for the first waving lotion and an oxidizing agent for the second neutralizing lotion. Moreover, since it is possible to provide the hair with wave without exerting influence upon disulfide linkages of the hair, the hair suffers no damage and also the waving effect can be maintained for a long term.

Also, the keratin hydrolyzate has the advantages that when applied to the hair, it does not give a feeling of a physical disorder because of being structurally similar to the hair, and does not make the hair stuffy because of having peptide linkages and having air-permeability, and is not charged with static electricity and the hair does not become dusty.

Any keratins constituting a wool, a feather, a hair, a horn, a hoof, etc. may be usable as a starting material for preparing the keratin hydrolyzate of the invention. Wool is particularly preferred, since it is easy to obtain.

Examples of the mercaptan employed as the reducing agent in the present invention are thioglycollic acid, cysteine, mercaptoethanol, thioglycerol and thiosalicylic acid. Examples of the sulfide employed as the reducing agent in the present invention are sodium sulfide, potassium sulfide, calcium sulfide, triethanolamine sulfide, diethanolamine sulfide and monoethanolamine sulfide.

In the present invention, protease capable of being activated under acidic conditions such as pepsine and protease capable of being activated under neutral condition such as bromelin, thermolysin, trypsin or chymotrypsin are employed as an enzyme for hydrolyzing the reduction product of keratin.

The water-soluble keratin hydrolyzate of the present invention is usually prepared as follows: Keratin is added to an aqueous solution of a reducing agent which is adjusted to alkaline conditions, and the reduction is carried out at a temperature of 0° to 40° C. for about 12 hours to about one week with agitation, preferably after passing a stream of an inert gas such as nitrogen through a reaction vessel to replace air in the vessel, so as to sever disulfide linkages of keratin and to form mercapto groups. In case of employing an alkaline reducing agent such as sulfides, it is not particularly necessary to add an alkaline material to the reaction system in order to maintain it basic. In case of employing an acidic or neutral reducing agent such as thioglycollic acid or mercaptoethanol, the reaction system is suitably maintained basic by adding an alkaline material such as sodium hydroxide or potassium hydroxide. In general, the reaction system is adjusted to pH 8 to 14. Also, urea may be added to the aqueous solution, since it swells the keratin and assists the reduction reaction. With the progress of the reaction, the keratin such as wool dissolves and pH of the reaction system lowers. In order to prevent the lowering of pH, a buffer such as tris(hydroxymethyl)aminomethane, ammonia or sodium bicarbonate may be added to the reaction system.

After the completion of the reduction reaction, the reaction mixture is filtered under reduced pressure to remove unreacted materials, and the filtrate is further subjected to ultrafiltration, by which the filtrate is concentrated to about ½ to about ¼ of its original volume. The thus obtained concentrated liquor is then subjected to dialysis by which, while the residual reducing agent is removed, the liquor is adjusted to pH suitable for enzymatic hydrolysis in the next stage.

After the dialysis, an enzyme is added to the liquor, and the hydrolysis is carried out, preferably at a temperature of 30° to 45° C., usually for 3 to 24 hours. When an enzyme capable of being activated under acidic conditions such as pepsine is employed, the liquor is preferably adjusted to pH 1 to 5, and when an enzyme capable of being activated under neutral condition such as bromelin is employed, the liquor is preferably adjusted to pH 5 to 8.

The molecular weight of the obtained hydrolysis product varies depending on the amount of the enzyme used, reaction time and reaction temperature. The optimum conditions of the enzymatic hydrolysis such as the amount of enzyme, reaction time and reaction temperature may be determined by measuring the distribution of molecular weight of the obtained hydrolysis product by means of a gelfiltration method. In the present invention, the hydrolysis is suitably controlled so as to give the hydrolyzate having an average molecular weight of 2,000 to 20,000. The keratin hydrolyzate having an average molecular weight of not less than 2,000 has at least two mercapto groups in one molecule, since keratin generally contains cystines in a proportion of about one cystine per 10 amino acids and also an average molecular weight of an amino acid in keratin is about 100. When the average molecular weight of the keratin hydrolyzate is more than 20,000, the hydrolyzate is water-insoluble and becomes difficult to handle.

The keratin hydrolyzate obtained in the form of an aqueous solution may be suitably concentrated, as occasion demands, by subjecting to ultrafiltration and concentration under reduced pressure. The keratin hydrolyzate is usually employed or stored in the form of an aqueous solution or a concentrated aqueous solution.

The keratin hydrolyzate of the present invention is particularly useful as hair fixatives, and can be formulated into various cosmetic compositions for fixing the hair.

In case of formulating the keratin hydrolyzate of the present invention into a permanent waving solution, an about 0.5% to about 6.0% by weight aqueous solution of the keratin hydrolyzate is prepared. This aqueous solution can be employed as a cold waving solution in place of a conventional cold waving solution consisting of a waving lotion for the first stage and a neutralizing lotion for the second stage. Into the aqueous solution of the hydrolyzate, there may be suitably incorporated water-soluble metal compounds such as iron gluconate as a catalyst, a surface active agent for increasing wetting of the hair, or a volatile alkaline substance such as ammonia. Waving of the hair is conducted by applying the cold waving solution thus prepared to the hair, winding the hair round rods and drying the hair by a drier to evaporate moisture. Upon drying the hair, application of a solution containing an oxidizing agent such as sodium bromate or hydrogen peroxide to the hair accelerates the oxidation of the keratin hydrolyzate and forms a high polymer film even at a low temperature.

In the use of the keratin hydrolyzate of the present invention in a set lotion, a composition is prepared by adding the keratin hydrolyzate in concentrations of about 0.5% to about 4% by weight to a mixed solvent of purified water and 5% to 10% by weight of an alcohol such as ethyl alcohol or isopropyl alcohol. There may be suitably incorporated into the composition conventionally employed ingredients in a set lotion, e.g. a plasticizer such as liquid paraffin or a water-soluble lanolin derivative, a softening agent such as glycerol or propylene glycol, a chelating agent, an antiseptic, a perfume, or a surface active agent.

The keratin hydrolyzate of the present invention may be employed in a conventional cold waving lotion for the first stage. The incorporation of the hydrolyzate into the lotion has the advantages that the alkalinity of the lotion can be lowered, and as a result, the damage of the hair and skin of the head can be decreased. Although the waving effect produced by a reducing agent such as thioglycollic acid or cysteine is decreased by the lowering of pH, this can be supplied by the keratin hydrolyzate of the invention and, therefore, as a whole there can be produced a waving effect of the same degree as that of the conventional first waving lotion adjusted to pH 9 to 10 and also the damage of the hair and skin of the head can be decreased in accordance with the decrease of the amount of an alkaline material.

The waving lotion for the first stage used in cold waving may be prepared by adding the keratin hydrolyzate of the invention in concentrations of about 0.3% to about 6.0% by weight to a purified water containing about 2% to about 7.5% weight of a usual reducing agent, e.g. thioglycollic acid, its salts such as ammonium thioglycolate, monoethanolamine thioglycolate and monoisopropanolamine thioglycolate, or cysteine, and then adjusting to pH 6 to 9 with, for instance, aqueous ammonia or ethanolamine. To the waving lotion may be suitably added usual other ingredients such as a penetrating agent, a chelating agent, a hair tonic, a hair dye, a perfume and a hair protective agent.

In addition to the above-mentioned uses, the keratin hydrolyzate of the present invention may be employed as a fundamental ingredient in the formulation of other cosmetic compositions intended for application to the hair, for instance, hair conditioners, hair dye compositions and hair straightener.

The present invention is more particularly described and explained by means of the following Examples, in which all % are by weight.

EXAMPLE 1

To a one liter beaker was added 480 g. of urea, and distilled water was then added until the total volume become about 900 ml. After substantially dissolving urea in water with stirring, 20 ml. of mercaptoethanol and 1 g. of ethylenediaminetetraacetic acid (hereinafter referred to as "EDTA") were added to the solution in the beaker. The solution was then adjusted to pH 8 with an aqueous solution of sodium hydroxide and was diluted to one liter in total volume with distilled water.

To the solution was added 20 g. of defatted wool, and after stirring the solution and removing generated foam, the beaker was covered and then allowed to stand at room temperature for 3 days with stirring sometimes. The resulting reaction mixture was filtered under reduced pressure to remove the unreacted wool.

The obtained filtrate (about 820 ml.) was subjected to ultrafiltration by employing an ultrafilter (commercially available under the tradename "402 Type Cell, Diaflow Membrane UM-10" made by Amicon) (fractionating molecular weight: 10,000). By the ultrafiltration, the concentration of the reaction product was increased, while the solvent containing urea and the reducing agent was filtered off. The filtrate was concentrated to 400 ml. The concentrated liquor was packed in a cellophane dialysis tube and was dialyzed for 8 hours against 5 liters of 0.1 N formic acid, and the dialysis for 8 hours against 5 liters of 0.1 N formic acid was further repeated twice.

The concentrated liquor subjected to dialysis was placed in a 500 ml. beaker, and thereto was added a solution of 40 mg. of pepsine dissolved in 4 ml. of 0.1 N acetic acid. The hydrolysis of keratin was then carried out at 37° C. for 8 hours with thoroughly stirring by a magnetic stirrer on a hot water bath. After the completion of the reaction, pepsine was inactivated by adjusting the reaction mixture to pH 7 with a 20% solution of sodium hydroxide by employing a pH meter, while cooling the beaker with ice.

The reaction mixture was then filtered under reduced pressure, and the filtrate was made acidic again by adding 2 ml. of acetic acid. The resulting solution was subjected to ultrafiltration by employing an ultrafilter (commercially available under the tradename "402 Type Cell, Diaflow Cell UM-2" made by Amicon) (fractionating molecular weight: 1,000) so as to desalt and to concentrate to 150 ml. The obtained concentrated liquor was placed in a 200 ml. eggplant type flask with ground stopper, and was concentrated under reduced pressure by employing a rotary evaporator to give a 20% aqueous solution of keratin hydrolyzate.

A part of the obtained aqueous solution of keratin hydrolyzate was taken out and was diluted with 0.1 N acetic acid to give a 0.5% aqueous solution of the keratin hydrolyzate. Three milliliters of the 0.5% aqueous solution was subjected to gelfiltration by employing "Sephadex G-50" made by Pharmacia Fine Chemicals AB (column volume: 260 cm.$^3$, column length: 50 cm., one fraction: 3.8 ml.). The concentration of peptide in each of the fractions of eluate obtained by the gelfiltration was determined by measuring absorbance at a wavelength of 230 nm. by employing an ultraviolet spectrophotometer. The results are shown in FIG. 1.

Figure 2:
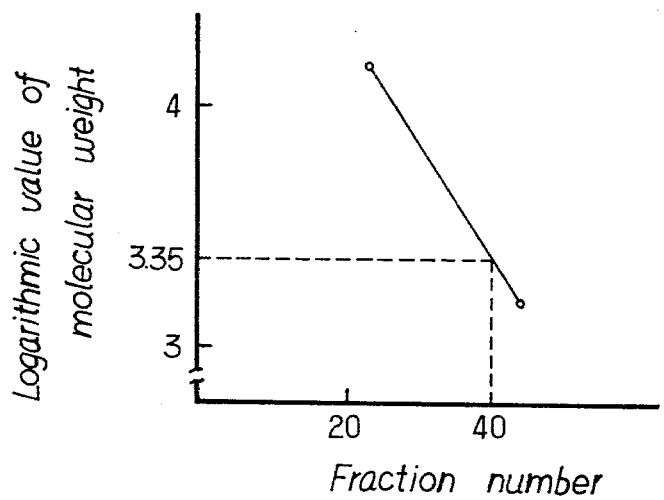
FIG. 2 is a graph showing the relationship between fractions of the eluate in gelfiltration of standard materials and logarithmic values of the molecular weights of the standard materials.

It is known that in a gelfiltration method, there is a straight-line relationship between the logarithmic value of the molecular weight of a material and the elution volume of the material. Although the fractionating molecular weight of the Sephadex G-50 was from 1,500 to 30,000, the gelfiltration was conducted under the same conditions as above with respect to sodium chloride and trypsin (molecular weight: 15,000). The fraction of sodium chloride appeared at fraction 44 and the fraction of trypsin appeared at fraction 23. From these results, a graph as shown in FIG. 2 was obtained.

In FIG. 1, the fraction showing the highest concentration of peptide was fraction 40. On the other hand, in FIG. 2, the logarithmic value of molecular weight corresponding to the fraction 40 was 3.35, and from this fact, it was determined that the molecular weight of peptide contained in the fraction appearing at fraction 40 was about 2,200.

Figure 3:
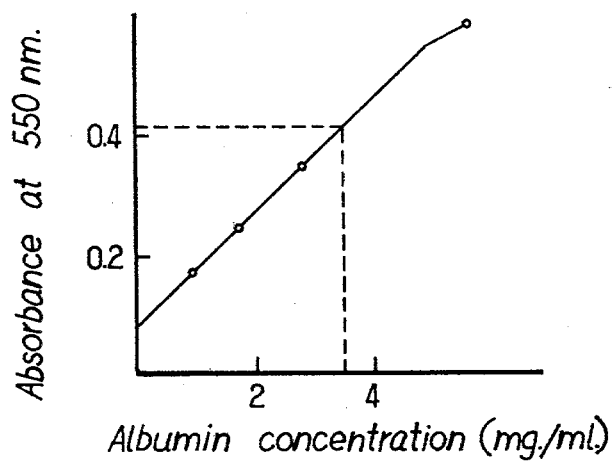
FIG. 3 is a graph showing the relationship between concentrations of albumin and absorbances at 550 nm.

The cysteine residues in the obtained keratin hydrolyzate were then determined as follows:

A part of the obtained 20% aqueous solution of keratin hydrolyzate was taken out and was diluted with 0.1 N acetic acid to give a 1% aqueous solution of keratin hydrolyzate. The aqueous solution was subjected to gelfiltration in the same manner as above, and the fractions appearing in the vicinity of the fraction 40 containing peptide having the molecular weight of about 2,200, i.e. the fractions appearing from fraction 38 to fraction 42 were collected. The peptide concentration of the collected fractions was measured by means of the following biuret method. To 1 ml. of the sample was added 4 ml. of biuret reagent, and after 30 minutes, the absorbance was measured at a wavelength of 550 nm. by means of a visible ray spectrophotometer. With respect to 4 samples of aqueous solutions of crystalline albumin of known concentrations (about 0.1% to about 0.5% aqueous solution) and distilled water, the same procedures as above were repeated to obtain a calibration curve shown in FIG. 3. The peptide concentrations obtained on the basis of the calibration curve was 3.62 mg./ml.

Figure 4:
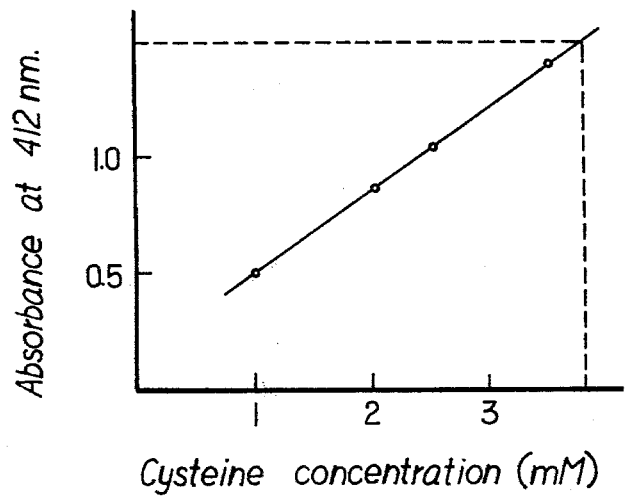
FIG. 4 is a graph showing the relationship between concentrations of cysteine and absorbances at 412 nm.

On the other hand, the cysteine concentration of the sample was also measured by the following Ellman method. A solution of 10 mg. of 5,5'-dithiobis(2-nitrobenzoic acid) dissolved in 2.5 ml. of 0.05 M phosphate buffer solution (pH 7.0) and 0.2 M sodium bicarbonate were prepared, and to 0.5 ml. of the sample were added 50 μl. of the solution of 5,5'-dithiobis(2-nitrobenzoic acid) and 2 ml. of 0.2 M sodium bicarbonate. After 10 minutes, absorbance was measured at a wavelength of 412 nm. by an ultraviolet spectrophotometer. With respect to aqueous solutions of cysteine by hydrochloride of known concentrations (0.1 mM to 10 mM), the same procedures as above were repeated to obtain a calibration curve shown in FIG. 4. The amount of mercapto groups of cysteine residues in the sample was obtained on the basis of the calibration curve, and as a result, it was determined that the cysteine residue concentration of the sample was 3.78 mM.

From the above both results of the determination of the peptide concentration and cysteine concentration, it became clear that peptide having the molecular weight of about 2,200 among the obtained keratin hydrolyzate contained mercapto groups corresponding to 12.6 g. of cysteine per 100 g. of the peptide, and as a result, peptide having the molecular weight of about 2,200 contained 2.3 mercapto groups per one peptide on the average.

In an insolubilization test, a water-insoluble polymer was partly produced by passing air at a rate of 5 cm.³/sec. through 5 g. of a 2% aqueous solution of keratin hydrolyzate. Measurement of the proportion of the insolubilized peptide by the biuret method indicated that 57% of peptide was insolublized in water and precipitated.

A 2% aqueous solution of the keratin hydrolyzate was applied to the hair, and the hair was wound round rods and dried by a drier to evaporate the moisture. Thereafter, the rods were removed from the hair. The hair had been adequately waved. After one week, the hair was washed with water, but the wave was maintained without any change.

By employing a 20% aqueous solution of the keratin hydrolyzate, a set lotion was prepared according to the following formulation.

| Ingredients | Amount (%) |
| --- | --- |
| Keratin hydrolyzate (solid) | 2 |
| Ethyl alcohol | 10 |
| EDTA (chelating agent) | 0.1 |
| Antiseptic | proper amount |
| Perfume | proper amount |
| Purified water | residue |
| | (total 100%) |

The set lotion was applied to the hair wound round curlers and dried for 5 minutes by a drier. The thus set hair was not sticky to the touch and was not stained with dust, and even after repeating washing-drying procedures 3 times, the hair maintained substantially the original state.

By employing a 20% aqueous solution of the keratin hydrolyzate, a waving lotion for use in the first stage of cold waving was prepared by admixing the following ingredients and adjusting to pH 7.5 with monoethanolamine.

| Ingredients | Amount (%) |
| --- | --- |
| Keratin hydrolyzate (solid) | 1.5 |
| Cysteine | 4.5 |
| Potassium salt of condensation product of coconut oil fatty acid and polypeptide derived from collagen | 1 |
| EDTA | 0.2 |
| Purified water | 92.8 |
| | (total 100%) |

The waving lotion was applied to the hair and was thoroughly made to permeate into the hair. After winding the hair round rods, the hair was covered with a cap and was allowed to stand for about 20 minutes. The cap was removed, and the hair wound around the rods was well washed with water. A 6% aqueous solution of sodium bromate was then applied to the hair as a neutralizing lotion and was thoroughly made to permeate into the hair, and the hair was allowed to stand for about 15 minutes to act sodium bromate on the hair.

The thus cold-waved hair maintained its state for about 2 months under usual conditions, and the waving lotion prepared according to the present invention was as effective as a conventional one adjusted to pH 9.5, despite that the waving lotion according to the present invention was pH 7.5.

EXAMPLE 2

To 1 liter of 1 M sodium thioglycolate adjusted to pH 10.5 with sodium hydroxide was added 35 g. of wool. After removing generated foam, air in a reaction vessel was replaced with nitrogen, and the mixture was allowed to stand at room temperature for 24 hours with stirring sometimes.

The resulting reaction mixture was filtered under reduced pressure to remove the unreacted material, and the obtained filtrate was subjected to ultrafiltration in the same manner as in Example 1 so as to concentrate to ⅓ time its original volume. The resulting concentrated liquor was packed in a cellophane dialysis tube, and was dialyzed for 6 hours against 3 liters of 0.1 N formic acid. This dialysis was repeated 3 times.

The concentrated liquor subjected to the dialysis was placed in a 500 ml. beaker, and thereto was added a solution of 20 mg. of pepsine dissolved in 2 ml. of 0.1 N acetic acid. The hydrolysis was carried out at 37° C. for 3 hours with stirring. The resulting reaction mixture was then concentrated under reduced pressure by employing a rotary evaporator on a hot water bath at 45° C. to nearly dryness. The thus obtained reaction product was added with 50 ml. of distilled water and dissolved. The solution was filtered under reduced pressure, and the filtrate was adjusted to pH 5 with an aqueous solution of sodium hydroxide to inactivate pepsine. Distilled water was then added to the filtrate to give a 20% aqueous solution of keratin hydrolyzate.

Average molecular weight of the keratin hydrolyzate was about 4,000, which was determined by conducting gelfiltration in the same manner as in Example 1. Also, as a result of the determination of the cysteine residue concentration by the Ellman method conducted in the same manner as in Example 1, peptide having the molecular weight of about 4,000 contained mercapto groups corresponding to 10.8 g. of cysteine per 100 g. of the peptide. From this result, it became clear that peptide having the molecular weight of about 4,000 contained 3.6 mercapto groups per one peptide on the average.

A 2% solution of the keratin hydrolyzate was applied to the hair, and the hair was wound round rods and dried by a drier to evaporate the moisture. Thereafter, the rods were removed from the hair. The hair was provided with adequate wave harder than that in Example 1. After one week, the hair was washed with water, but the wave was maintained without any change.

By employing a 20% aqueous solution of the keratin hydrolyzate, a set lotion was prepared according to the following formulation.

| Ingredients | Amount (%) |
|---|---|
| Keratin hydrolyzate (solid) | 2 |
| Polypeptide derived from collagen (average molecular weight: about 2,000) | 1.5 |
| Ethyl alcohol | 10 |
| EDTA (chelating agent) | 0.1 |
| Antiseptic | proper amount |
| Perfume | proper amount |
| Purified water | residue (total 100%) |

The set lotion was applied to the hair wound round curlers and dried for 5 minutes by a drier. The thus set hair was not sticky to the touch and was not stained with dust, and even after repeating washing-drying procedures 3 times, the hair maintained substantially the original state.

By employing a 20% aqueous solution of the keratin hydrolyzate, a waving lotion for use in the first stage of cold waving was prepared by admixing the following ingredients and adjusting to pH 7.8 with ammonia water.

| Ingredients | Amount (%) |
|---|---|
| Keratin hydrolyzate (solid) | 2 |
| Ammonium thioglycolate | 5 |
| Polypeptide derived from collagen | 3 |
| Polyoxyethylenesorbitan monooleate | 1 |
| EDTA | 0.2 |
| Purified water | 88.8 (total 100%) |

The waving lotion was applied to the hair and was thoroughly made to permeate into the hair. After winding the hair round rods, the hair was covered with a cap and was allowed to stand for about 20 minutes. The cap was removed, and the hair wound round the rods was well washed with water. A 6% aqueous solution of sodium bromate was then applied to the hair as a neutralizing lotion and was thoroughly made to permeate into the hair, and the hair was allowed to stand for about 15 minutes to act sodium bromate on the hair.

The thus cold-waved hair maintained its state for about 2 months under usual conditions, and the waving lotion prepared according to the present invention was as effective as a conventional one adjusted to pH 9.6, despite that the waving lotion according to the present invention was pH 7.8.

EXAMPLE 3

To one liter of 0.5 M sodium sulfide containing 0.1% of EDTA was added 35 g. of wool, and after removing generated foam, the mixture was allowed to stand for 24 hours with stirring sometimes.

The resulting reaction mixture was then filtered under reduced pressure to remove the unreacted material, and the filtrate was subjected to ultrafiltration in the same manner as in Example 1 so as to concentrate to ⅓ time its original volume. The resulting concentrated liquor was packed in a cellophane dialysis tube, and was dialyzed for 6 hours against 3 liters of distilled water. This dialysis was repeated 3 times.

The concentrated liquor subjected to the dialysis was placed in a beaker, and after adjusting to pH 5 with acetic acid by employing a pH meter, 200 mg. of bromelin (500 thousand units/g.) and 20 mg. of cysteine hydrochloride were added to the liquor. The hydrolysis was carried out at 40° C. for 10 hours with stirring. After the completion of the hydrolysis, the reaction mixture was heated to 70° C. to inactivate the bromelin. The obtained reaction mixture was then filtered under reduced pressure, and after adding 2 ml. of acetic acid to the resulting filtrate to make it acidic, the filtrate was subjected to ultrafiltration in the same manner as in Example 1 to desalt and to concentrate to 150 ml. The obtained concentrated liquor was further concentrated under reduced pressure by employing a rotary evaporator to give a 20% aqueous solution of keratin hydrolyzate.

Average molecular weight of the obtained keratin hydrolyzate was about 3,300, which was determined by conducting gelfiltration in the same manner as in Example 1. Also, as a result of the determination of the cysteine residue concentration by the Ellman method conducted in the same manner as in Example 1, peptide having the molecular weight of about 3,300 contained mercapto groups corresponding to 10.8 g. of cysteine per 100 g. of the peptide. From this result, it became clear that peptide having the molecular weight of about 3,300 contained 2.9 mercapto groups per one peptide on the average.

A 2% aqueous solution of the keratin hydrolyzate was admixed with a 0.1% aqueous solution of iron gluconate, and the mixture was immediately applied to the hair. The hair was wound round rods, and was dried by a drier to evaporate the moisture. Thereafter, the rods were removed from the hair. The hair was provided with adequate wave. After one week, the hair was washed with water, but the wave was maintained without any change.

What we claim is:

1. A process for preparing a water-soluble keratin hydrolyzate which comprises reducing keratin in an aqueous solution of a reducing agent selected from the group consisting of mercaptans and sulfides under alkaline conditions, removing the reducing agent from the resulting reduction product and then subjecting the reduction product to enzymatic hydrolysis in an aqueous medium in the presence of an enzyme capable of hydrolyzing protein, to give a water-soluble keratin hydrolyzate having at least two mercapto groups in one molecule and having an average molecular weight of 2,000 to 20,000.

2. The process of claim 1, wherein pH of said aqueous solution of a reducing agent is from 8 to 14.

3. The process of claim 1, wherein said mercaptans are selected from the group consisting of thioglycollic acid, cysteine, mercaptoethanol, thioglycerol and thiosalicylic acid.

4. The process of claim 1, wherein said sulfides are selected from the group consisting of sodium sulfide, potassium sulfide, calcium sulfide, triethanolamine sulfide, diethanolamine sulfide and monoethanolamine sulfide.

5. The process of claim 1, wherein the reduction of keratin is carried out at a temperature of 0° to 40° C.

6. The process of claim 1, wherein said enzyme is selected from the group consisting of pepsine, bromelin, thermolysin, trypsin and chymotrypsin.

7. The process of claim 1, wherein said enzymatic hydrolysis is carried out at a temperature of 30° to 45° C.

* * * * *